(12) United States Patent
Chu et al.

(10) Patent No.: US 9,029,050 B2
(45) Date of Patent: May 12, 2015

(54) METHOD FOR REPAIRING A MASK

(71) Applicant: Taiwan Semiconductor Manufacturing Company, Ltd., Hsin-Chu (TW)

(72) Inventors: Fu-Sheng Chu, Zhubei (TW); Yuan-Chih Chu, New Taipei (TW)

(73) Assignee: Taiwan Semiconductor Manufacturing Company, Ltd., Hsin-Chu (TW)

( * ) Notice: Subject to any disclaimer, the term of this patent is extended or adjusted under 35 U.S.C. 154(b) by 0 days.

(21) Appl. No.: 13/895,011

(22) Filed: May 15, 2013

(65) Prior Publication Data

US 2014/0268119 A1    Sep. 18, 2014

Related U.S. Application Data

(60) Provisional application No. 61/777,965, filed on Mar. 12, 2013.

(51) Int. Cl.
*G03F 1/72* (2012.01)
*G01N 21/956* (2006.01)

(52) U.S. Cl.
CPC ............... *G03F 1/72* (2013.01); *G01N 21/956* (2013.01)

(58) Field of Classification Search
USPC ......................................... 430/5, 30; 382/144
See application file for complete search history.

(56) References Cited

U.S. PATENT DOCUMENTS 8,189,203 B2 *  5/2012  Shmarev et al. .............. 356/511

* cited by examiner

*Primary Examiner* — Christopher Young
(74) *Attorney, Agent, or Firm* — Haynes and Boone, LLP

(57) ABSTRACT

The present disclosure provides a method of repairing a mask. The method includes inspecting the mask using a mask inspection tool to identify a defect on a circuit pattern of the mask; repairing the defect using a mask repair tool to form a repaired pattern; forming a first group of diffraction images of the repaired pattern and a second group of diffraction images of a reference feature; and validating the mask by comparing the first group of diffraction images with the second group of diffraction images.

20 Claims, 13 Drawing Sheets

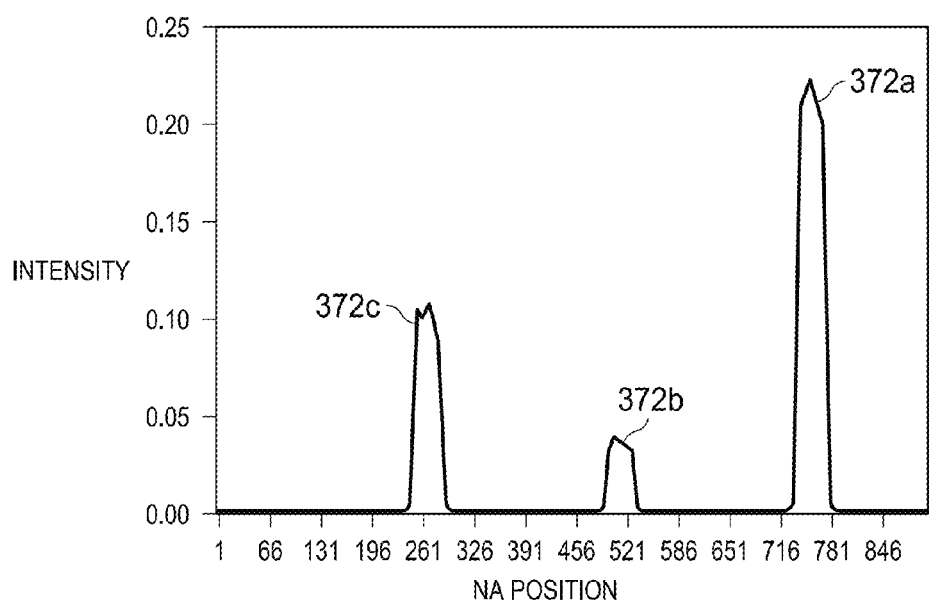

METHOD FOR REPAIRING A MASK

PROVISIONAL REFERENCE

This application claims the benefit of U.S. Provisional Application 61/777,965 entitled "A METHOD FOR REPAIRING A MASK," filed Mar. 12, 2013, herein incorporated by reference in its entirety.

BACKGROUND

The semiconductor integrated circuit (IC) industry has experienced exponential growth. Technological advances in IC materials and design have produced generations of ICs where each generation has smaller and more complex circuits than the previous generation. In the course of IC evolution, functional density (i.e., the number of interconnected devices per chip area) has generally increased while geometry size (i.e., the smallest component or line that can be created using a fabrication process) has decreased. This scaling down process generally provides benefits by increasing production efficiency and lowering associated costs. Such scaling down has also increased the complexity of processing and manufacturing ICs and, for these advances to be realized, similar developments in IC processing and manufacturing are needed. In one example associated with lithography patterning, a photomask (or mask) to be used in a lithography process has a circuit pattern defined thereon and is to be transferred to wafers. The pattern on the mask needs to be more accurate and the lithography patterning is more sensitive to the mask defects for small feature sizes in the advanced technology nodes. Accordingly, a mask is repaired to eliminate defects and is further checked to validate the repaired defects.

BRIEF DESCRIPTION OF THE DRAWINGS

The present disclosure is best understood from the following detailed description when read with accompanying figures. It is emphasized that, in accordance with the standard practice in the industry, various features are not drawn to scale and are used for illustration purpose only. In fact, the dimension of the various features may be arbitrarily increased or reduced for clarity of discussion.

FIGS. 7A-7C illustrate another embodiment of validating a repaired feature on a mask.

DETAILED DESCRIPTION

Figure 1:
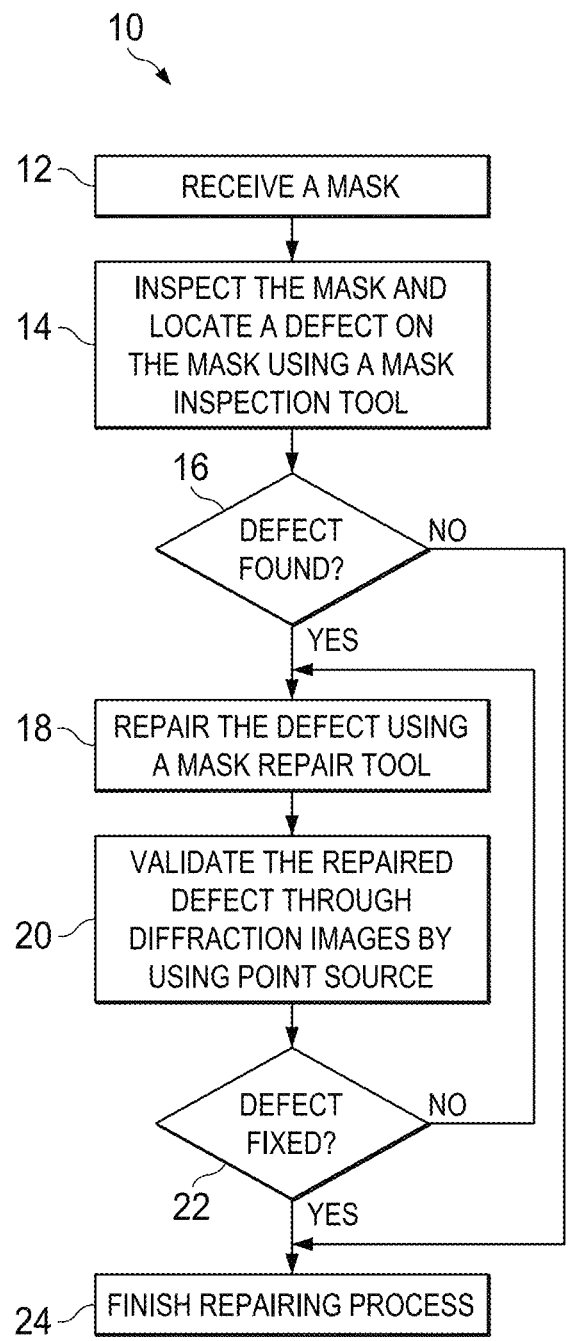
FIG. 1 is a flowchart of a method for repairing a mask according to one or more embodiments of the present invention.

The following disclosure provides many different embodiments, or examples, for implementing different features of the disclosure. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

FIG. 1 is a flowchart of a method 10 of repairing a defect in a mask substrate constructed according to various aspects of the present disclosure in one or more embodiments. The method 10 is described with reference to FIG. 1 and other figures. The mask repairing may be implemented in a mask shop for making a mask, in a fab for fabricating a semiconductor device on a wafer using a mask, or in a glass factory for manufacturing a mask blanket. It is understood that additional steps can be provided before, during, and after the method 10, and some of the steps described can be replaced, eliminated, or moved around for additional embodiments of the method 10. The method 10 is only an exemplary embodiment, and is not intended to limit the present invention beyond what is explicitly recited in the claims.

The method 10 begins at 12 by receiving or providing a mask. The mask is used to fabricate semiconductor wafers during lithography processes. The mask includes a substrate and a pattern formed on or to be formed on the substrate. The pattern is defined according to a circuit design.

Figure 2:
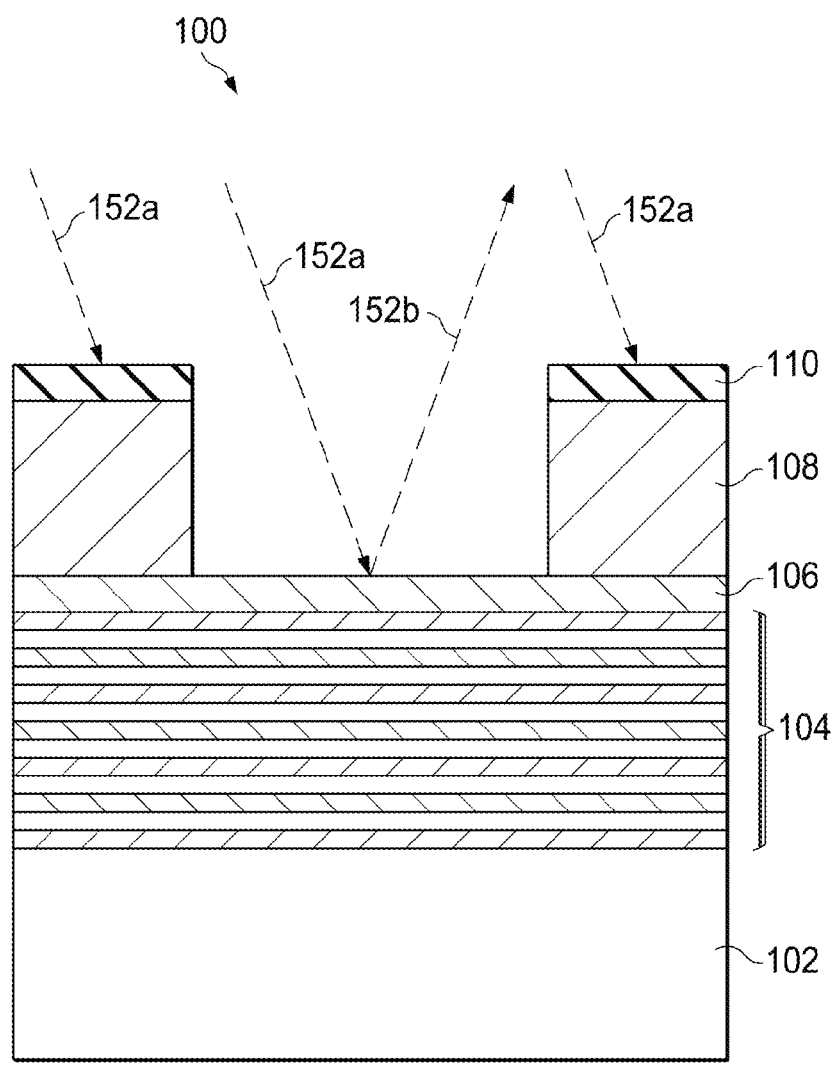
FIG. 2 is a sectional view of a reflective photomask (or reticle or mask) used in an extreme ultraviolet (EUV) lithography exposing tool that can benefit from one or more embodiments of the present disclosed method.

In some embodiments, a mask is a reflective mask to be used in an extreme ultraviolet (EUV) lithography. An exemplary reflective mask 100 is illustrated in FIG. 2 in a sectional view. The reflective mask 100 includes a substrate 102, a reflective multilayer (ML) 104 deposited on the substrate 102, a capping layer 106 deposited on the reflective ML 104, a patterned absorber layer 108 deposited on the capping layer 106, and a protection layer 110 deposited on the patterned absorber layer 108. It is understood that other configurations and inclusion or omission of various items in the mask 100 may be possible.

In some embodiments, the substrate 102 may include low thermal expansion material (LTEM). The substrate 102 serves to minimize image distortion due to mask heating by the intensified illumination radiation. The LTEM may include fused silica, fused quartz, calcium fluoride ($CaF_2$), silicon carbide, silicon oxide-titanium oxide alloy and/or other suitable LTEM known in the art. The substrate 102 includes materials with a low defect level and a smooth surface.

The reflective ML 104 is deposited on the substrate 102. According to Fresnel equations, light reflection occurs when light propagates across the interface between two materials of different refractive indices. The reflected light is greater when the difference of refractive indices is greater. To increase the reflected light, one may also increase the number of interfaces by depositing the reflective ML 104 of alternating materials and let light reflected from different interfaces interfere constructively by choosing appropriate thicknesses for each layer inside the reflective ML 104. However, the absorption of the employed materials for the reflective ML 104 limits the highest reflectivity that can be achieved. The reflective ML 104 includes a plurality of film pairs, such as molybdenum-silicon (Mo/Si) film pairs (e.g., a layer of molybdenum above or below a layer of silicon in each film pair). Alternatively, the reflective ML 104 may include molybdenum-beryllium (Mo/Be) film pairs, or any material that is highly reflective at EUV wavelengths can be utilized for the reflective ML 104. The thickness of each layer of the reflective ML 104 depends on the EUV wavelength and the incident angle. The thickness of the reflective ML 104 is adjusted to achieve a maximum constructive interference of the EUV light reflected at each interface and a minimum absorption of the EUV light by the reflective ML 104. The reflective ML 104 may be selected such that it provides a high reflectivity to a selected radiation type/wavelength. A typical number of film pairs are 20-80, however any number of film pairs is possible. In some embodiments, the reflective ML 104 includes forty pairs of layers of Mo/Si. In one example, each Mo/Si film pair has a thickness of about 7 nm, with a total thickness of 280 nm, and thereby a reflectivity of about 70% is achieved.

The capping layer 106 is deposited on the reflective ML 104. Because the capping layer 106 has different etching characteristics from an absorber layer, the capping layer 106 acts as an etch stop layer in a subsequent patterning or a repairing process of the absorber layer, which will be described later. The capping layer 106 includes ruthenium (Ru) or Ru compounds such as ruthenium-boron (RuB) or ruthenium-silicon (RuSi).

The absorber layer 108 is deposited on the capping layer 106 and then is patterned to form the main pattern according to an IC design layout. In some embodiments, the absorber layer 108 absorbs a radiation beam projected on it. The absorber layer 108 can include a single layer or multiple layers from a group of chromium (Cr), chromium oxide (CrO), titanium nitride (TiN), tantalum nitride (TaN), tantalum (Ta), titanium (Ti), or aluminum-copper (Al—Cu), palladium, tantalum boron nitride (TaBN), aluminum oxide (AlO), molybdenum (Mo), or other suitable materials.

The protection layer 110 may be deposited on the absorber layer 108. In some embodiments, the protection layer 110 may protect the absorber layer 108 from an oxidation of the high absorbing material when the mask is in a cleaning process. Furthermore, some of the absorber layer 108 has poor clean resistance and the protection layer 110 can enhance the cleaning durability.

As shown in FIG. 2, when an illumination beam 152a is projected on the mask 100, a portion of the illumination beam 152a projected on the absorber layer 108 is absorbed by the absorber layer 108 and another portion of the illumination beam 152a projected on the reflective ML 104 is reflected by the reflective ML 104. A patterned illumination bean 152b is thereby generated. The patterned illumination beam 152b is used to expose a resist film deposited on a wafer substrate and a resist pattern is formed on the wafer substrate. Forming a resist pattern on a wafer substrate will be discussed in more detail below.

One challenge of using a reflective EUV lithography technique occurs when a defect appears in/on a reflective EUV mask. While a relatively small defect may not be significantly detrimental when using a transmissive mask, a similar defect may be significant when using a reflective EUV mask. For example, a defect in a reflective ML may change or distort a reflected illumination beam in direction, shape, or phase. Therefore, a quality or integrity of the corresponding exposed image is impacted by the defect located in the reflective ML of the reflective EUV mask. In some embodiments, a defect in a reflective ML of a reflective EUV mask is also referred to as a phase defect. A mask defect is further described below.

Figure 3A:
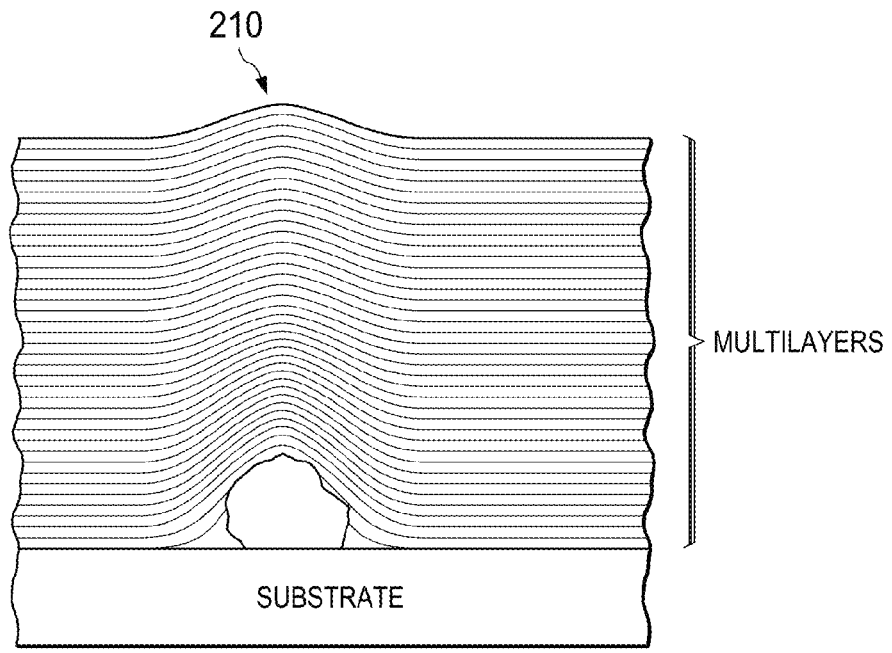
FIGS. 3A and 3B are sectional views of an exemplary defect in a reflective mask constructed according to various embodiments.
Figure 3B:
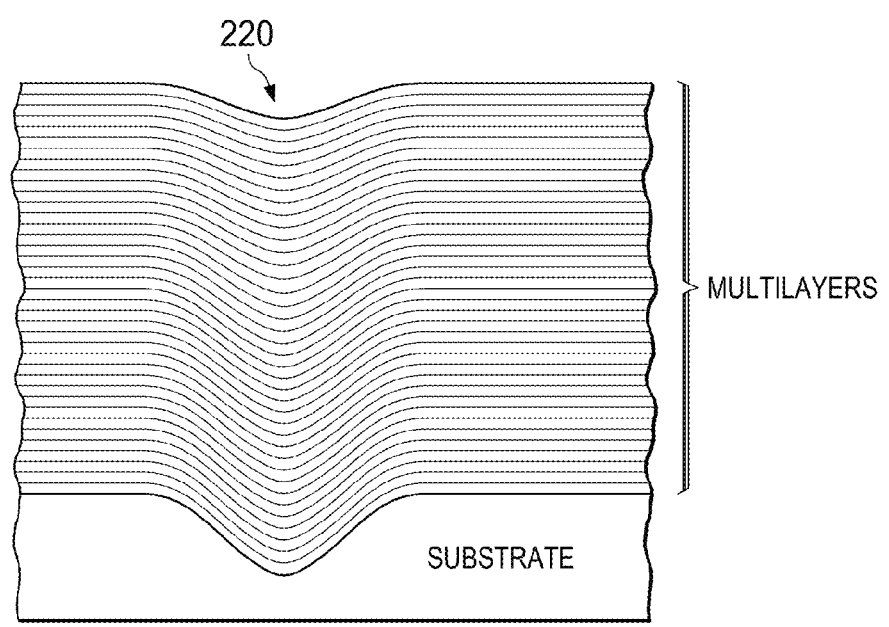

FIGS. 3A and 3B illustrate a defect in a reflective mask according to various examples. In one example, a bump defect 210 is illustrated in FIG. 3A. In another example, a pit defect 220 is illustrated in FIG. 3B. Either the bump defect 210 or the pit defect 220 changes profile of the multilayer surface and therefore distorts the reflected illumination beam from the multilayer surface.

Figure 4:
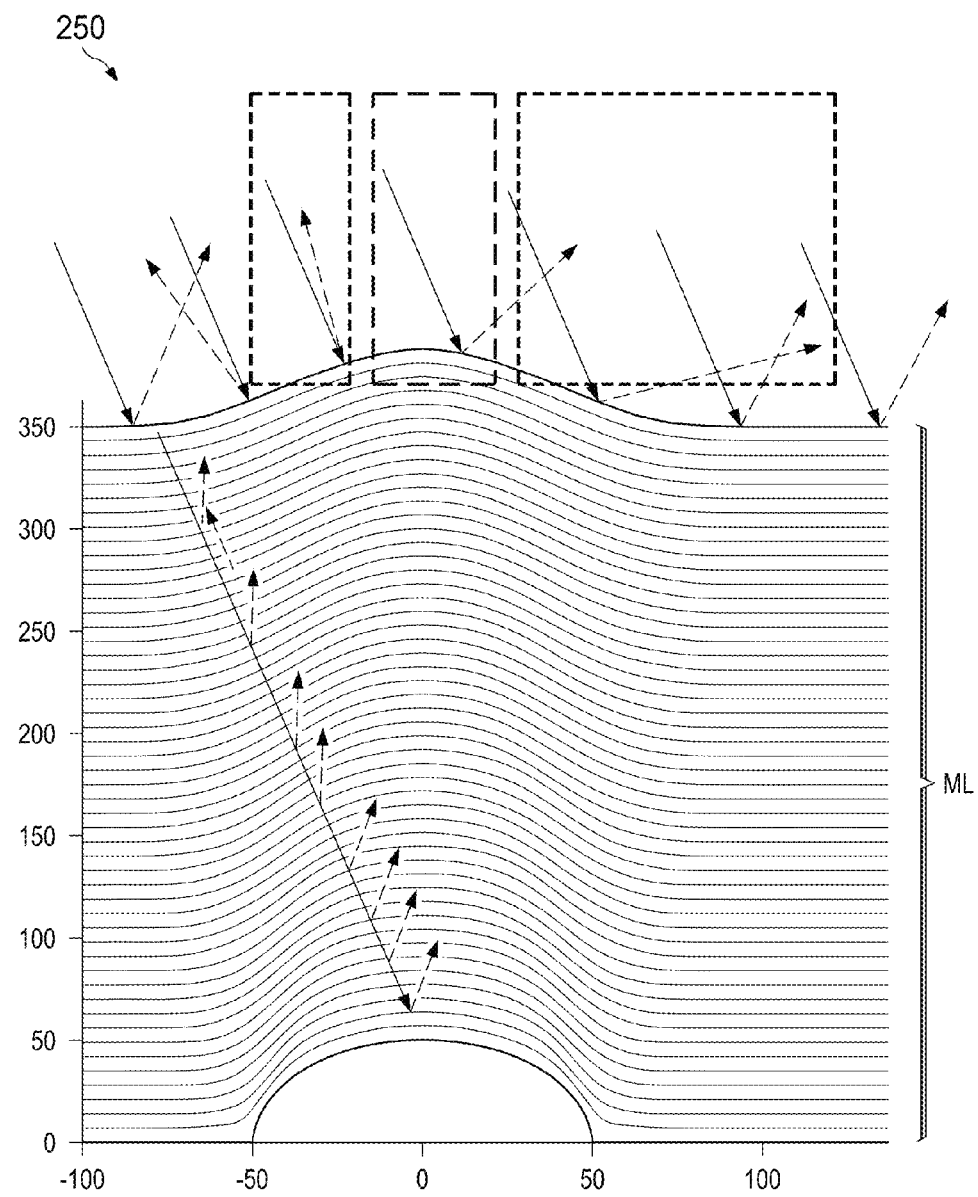
FIG. 4 is illustrates illuminating a reflective mask during a lithography process constructed according to one embodiment.

Referring now to FIG. 4, an example 250 of the illumination beam reflected on the multilayer surface of a reflective mask having a defect is illustrated. The defect includes a bump defect in the multilayer. The incident illumination beam is presented as a solid arrow line and the reflected illumination beam is represented as a dash arrow line. The bump defect creates an irregular surface on the multilayer. The irregular surface may create a plurality of irregular reflected illumination beams because of the phased effect and the scattering effect.

Figure 5A:
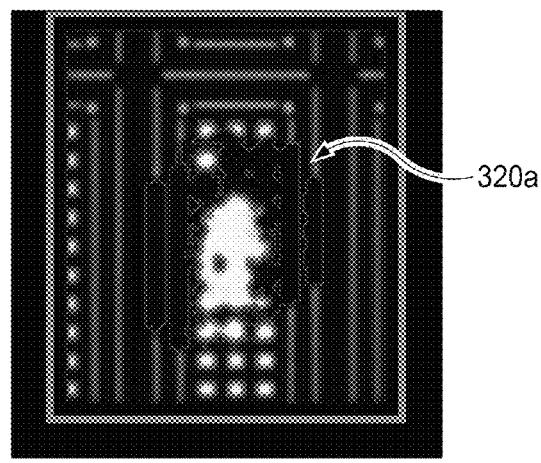
FIGS. 5A-5C illustrate examples of repairing an EUV mask.
Figure 5B:
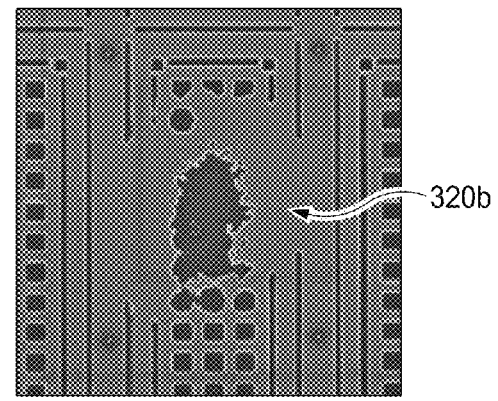

Now back to FIG. 1, the method 10 includes an operation 14 by inspecting the mask to identify a defect using a mask inspection tool, such as an optical inspection tool or an atomic force microscope (AFM). Inspecting the mask includes scanning a surface of the mask, locating a defect on the mask, and determining the shape and the size of the defect. FIG. 5A illustrates a defect 320a located by an optical inspection tool, and FIG. 5B includes a scanning electron microscope (SEM) image of the defect 320b in a top view.

The method 10 may proceed to an operation 16 by evaluating the mask inspection result. Evaluating the mask inspection may also include running a simulation to determine an impact of the defect on a resist pattern to be printed or formed on a wafer substrate. If the defect is small and within the specification (for example, the defect is smaller than 3 nm in height or roughness), the mask is considered as defect free and the method 10 proceeds to 24 to finish the repairing process. If the defect is out of the specification, for example, larger than 3 nm in height or roughness, the mask is considered to have a defect and the defect needs to be repaired.

Figure 5C:
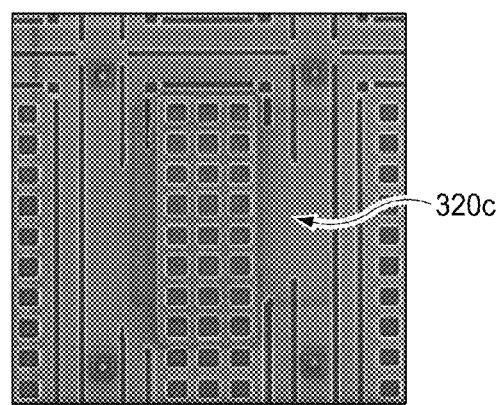

The method 10 proceeds to an operation 18 by repairing the defect using a mask repairing tool. In some embodiments, repairing the defect includes using a radiation beam, such as an electron beam or an ion beam to heat the bump defect and smooth the bump defect and the surrounding area. In other embodiments, repairing the defect includes scooping the pit defect and depositing a patch by a deposition process, such as a chemical vapor deposition (CVD). FIG. 5C illustrates a top view SEM picture of a mask with a repaired defect 320c.

The method 10 proceeds to an operation 20 by validating the repaired defect that includes checking if the defect is fixed. In some embodiments, the validating includes performing a simulation process to evaluate the real impact of the repaired mask on a silicon wafer.

In some embodiments, the repaired defect includes acquiring aerial images of the repaired defect and the reference feature on an AIMS tool by emulating an illumination condition of an exposing tool, applying an after development inspection (ADI) CD target on the aerial image of the reference feature to get a target threshold, and measuring the CD on the aerial image of the repaired defect through focus.

Performing the simulation also includes comparing the CD difference between the repaired defect and a reference feature.

Figure 6A:
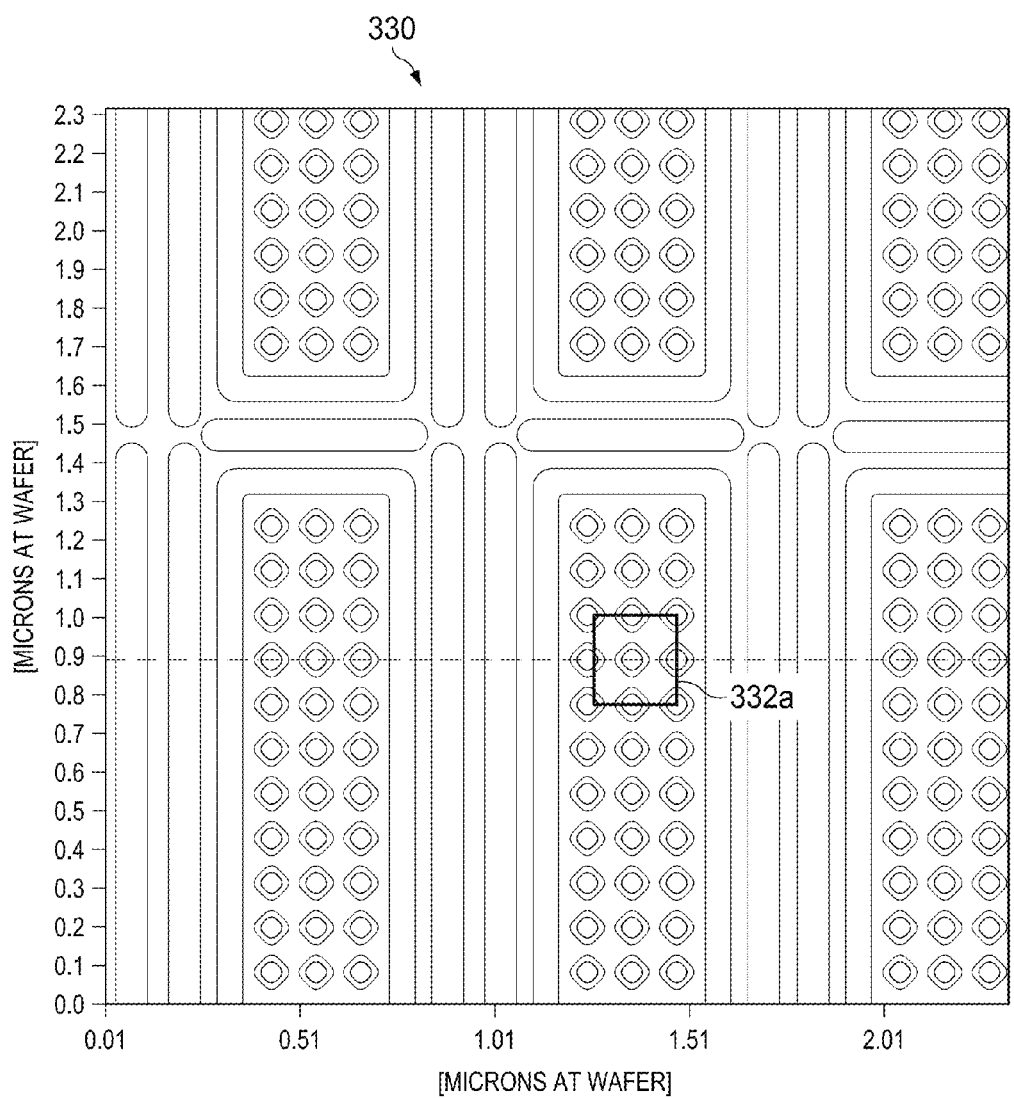
FIGS. 6A-6C illustrate one embodiment of validating a repaired feature on a mask.
Figure 6B:
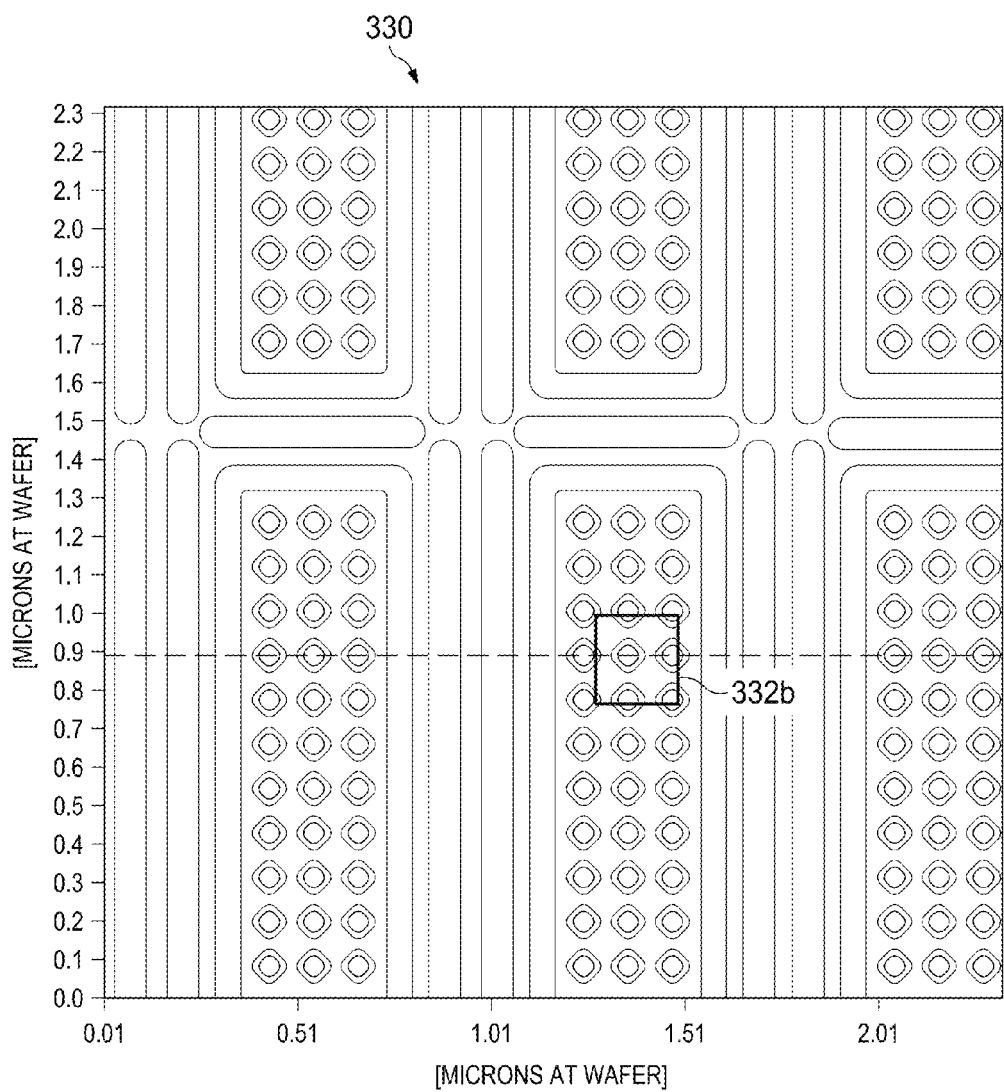
Figure 6C:
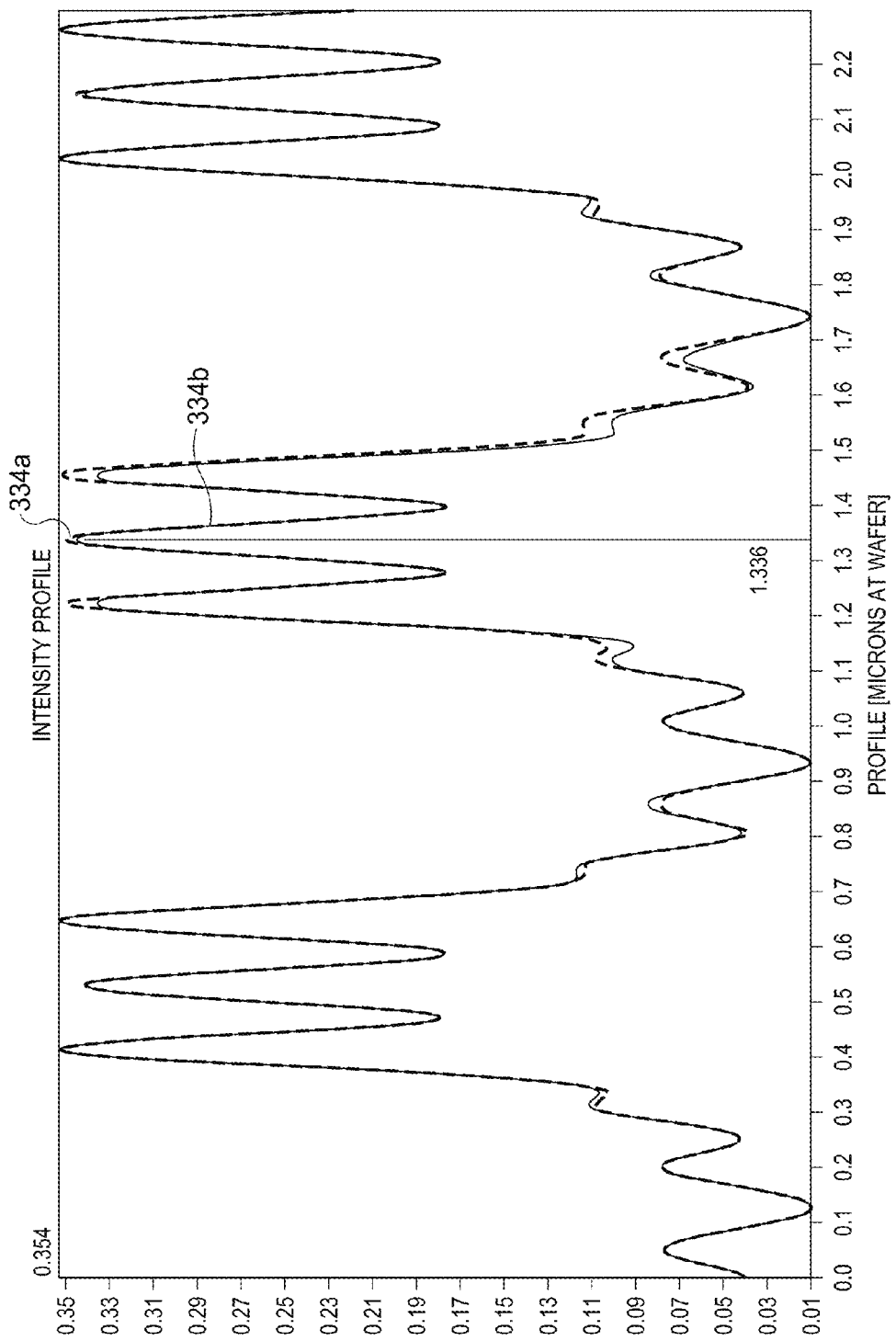

Illustrated in FIGS. 6A-C are examples of validating the repaired defect on a mask 330. The mask 330 includes a repaired feature 332a, a reference feature 332b, a first aerial image profile 334a from the repaired feature 332a, and a second aerial image profile 334b from the reference feature 332b. The second aerial image profile 334b at position 1.336 µm is from a reference feature having 60 nm CD target. In some embodiments, a measurement threshold 0.264 is obtained for measuring the reference feature having 60 nm CD using the second image profile 334b and the measured CD is 55 nm for the repaired feature 332a at position 1.336 µm of the first aerial image profile 334a using the threshold 0.264. 55 nm CD is within specification limit (e.g. ±10%) for 60 nm CD. In some embodiments, there is no separated information and correlation between mask and optical part (e.g. illumination source) that would cause uncertainty from the aerial image CD validation. Further, exposure latitudes of the repaired defect are much different from the different illumination sources.

In other embodiments, the validating includes acquiring diffraction image(s) of the repaired defect and the reference feature (e.g. a layout from a design database or a similar a defect-free feature on the mask) using a point source and evaluating the repaired defect based on the diffraction image (s). From the diffraction images, it is able to extract more information of the repaired defect to validating analysis. Particularly, 3 dimensional (3D) imaging data of a feature can be extracted from the diffraction images for more effective validating analysis.

A 3D effect of a feature on the mask can be described by two characteristic terms of a diffraction image of the feature, such as intensity (or amplitude) and numeric aperture (NA) position of different diffraction order from a pupil image. In some embodiments, a repaired feature on the mask is evaluated using the acquired or measured diffraction image of the repaired feature. Specifically, validating the repaired defect is executed by comparing diffraction images at various orders (DO images) between the repaired feature and the reference feature.

Figure 7A:
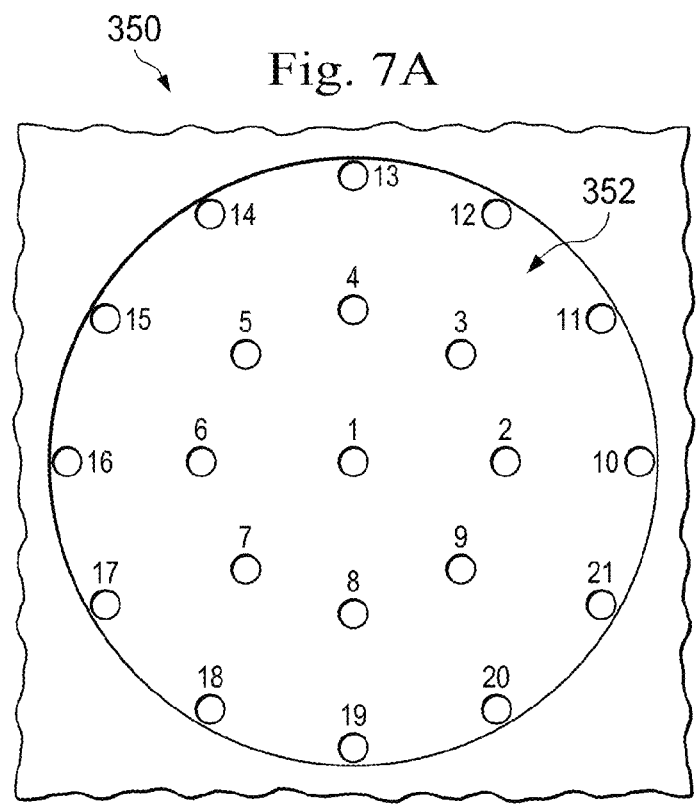

The validation of the repaired defect at operation 20 is further described below. The validating includes acquiring a diffraction image of the repaired features using an imaging system, such as an AIMS system, scanner or other suitable imaging system. FIG. 7A illustrates an aperture (or pupil) 350 to be used in acquiring various diffraction images during validating the repaired defect in accordance with various embodiments of the present disclosure. The aperture 350 is designed to have a plurality of point openings 352 used to provide one or more point sources for diffraction images. When imaging the repaired feature or the reference feature, the aperture 350 is configured in the imaging system such that the light only passes through one point (serving as point source) while other point openings are blocked. The point openings 352 are configured at various locations (with different off-center distance and different orientation). In the present example, the point openings 352 include 21 point openings as labeled in FIG. 7A.

Figure 7B:
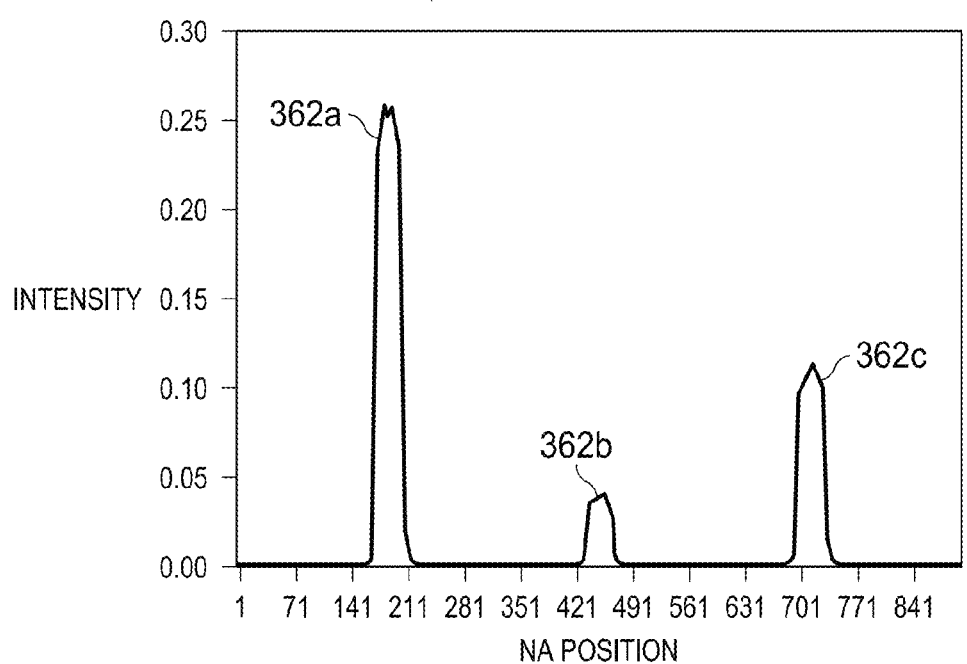

By imaging the repaired feature using one point source, the corresponding diffraction image 360 (or DO images 360) is acquired, as illustrated in FIG. 7B. In this example, the DO images 360 include a zero order image 362a, a first order image 362b, and a second order image 362c. Each DO image is characterized by its intensity I and numerical aperture NA. NA is defined $NA = n*\sin(\theta)$ where n is the corresponding refractive index and theta is angle of the corresponding DO image relative to the optical axis. In the present example, the DO images 360 include the zero order image 362a, the first order image 362b, and the second order image 362c with respective intensities and numerical apertures ($NA_0$, $I_0$), ($NA_1$, $I_1$), and ($NA_3$, $I_3$).

Similarly, by imaging the reference feature using the same point source, the corresponding diffraction image 370 (or DO images 370) is acquired, as illustrated in FIG. 7C. In this example, the DO images 370 include a zero order image 372a, a first order image 372b, and a second order image 372c with respective intensities and numerical apertures.

In some embodiments, the DO images for the repaired feature (and the DO images for the reference feature as well) may include two or more diffraction images acquired by using two or more different point sources. In other embodiments, the DO images include two diffraction images acquired by using a pair of symmetrical point sources such as point sources 10 and 16.

Back to FIGS. 7B and 7C, in some embodiments, the DO images 360 (or the DO images 370) include two or more diffraction images acquired by using two or more respective point sources, such as a pair of symmetrical point sources 10 and 16. According to one or more embodiments, the DO images of the repaired feature are similar to those of the reference feature. For example, the zero order image 362a of the repaired feature is similar to the zero order image 372a of the reference feature, the first order image 362b of the repaired feature is similar to the first order image 372b of the reference feature, and the second order image 362c of the repaired feature is similar to the second order image 372c of the reference feature. The differences therebetween are used to validate the repaired defect.

The method 10 proceeds to an operation 22 by evaluating if the defect is repaired. If the difference between the repaired feature and the reference feature is within predefined criteria, such as specification of a mask shop or a fab, the defect is considered to be repaired. If the difference between the repaired feature and reference is out of specification of the mask shop or the fab, the defect is not repaired. The mask needs to be reworked. For example, the mask goes back to operation 18 again by repairing the defect and then to operation 20 by performing a validating process on the repaired feature. This procedure may be repeated for a multiple times until the defect is repaired.

The method 10 proceeds to an operation 24 by finishing repairing process. Finishing repairing process may include mounting a frame and pellicle at pattern side of the mask to protect the pattern. Finishing repairing process may also include packing the mask and shipping the mask to a fab to fabricate an IC device.

Figure 8:
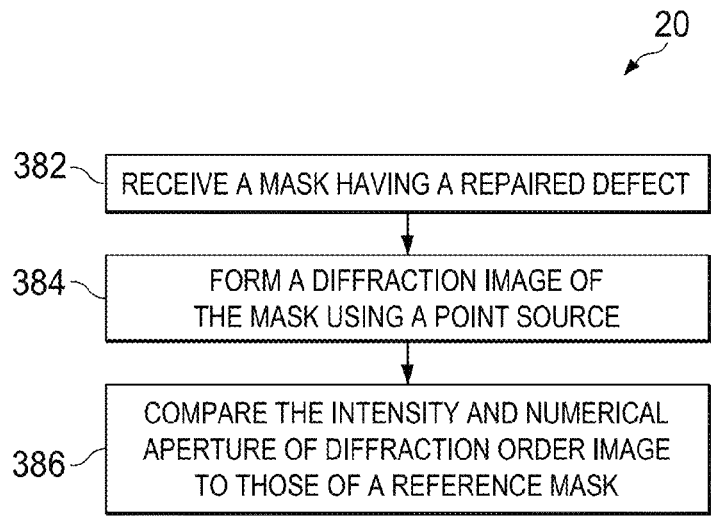
FIG. 8 is a flowchart of a method for validating a repaired mask according to one or more embodiments of the present disclosure.

The operation (or method) 20 of the method 10 is further described with a flowchart in FIG. 8 according to one or more embodiments. The method 20 begins at 382 by receiving a repaired defect. The method 20 proceeds to a step 384 by forming DO images of the repaired feature and forming DO images of the reference feature using a point source.

The method 20 includes a step 386 of comparing the intensities and numerical apertures of the DO image of the repaired feature to the respective intensities and numerical apertures of the diffraction image of the reference feature according to predefined criteria, such as a specification. If the differences of the respective intensities and the numerical apertures between the repaired feature and the reference feature are within the specification, it is considered as repaired or valid repair. Otherwise, it is considered as not repaired or invalid repair.

In other embodiments, step 384 includes forming DO images from a second diffraction image of the repaired feature and forming corresponding DO images of the reference feature using another point source. Then the step 386 includes further comparing based on the DO images from the second diffraction image.

In other embodiments, step 384 includes forming DO images of the repaired feature and forming corresponding DO images of the reference feature using two or more point sources.

In other embodiments, a subset of point sources is chosen according to various factors, such as sensitivity. At step 384, the DO images are formed by using the subset of corresponding point openings while the rest point openings of the aperture are blocked.

Figure 9:
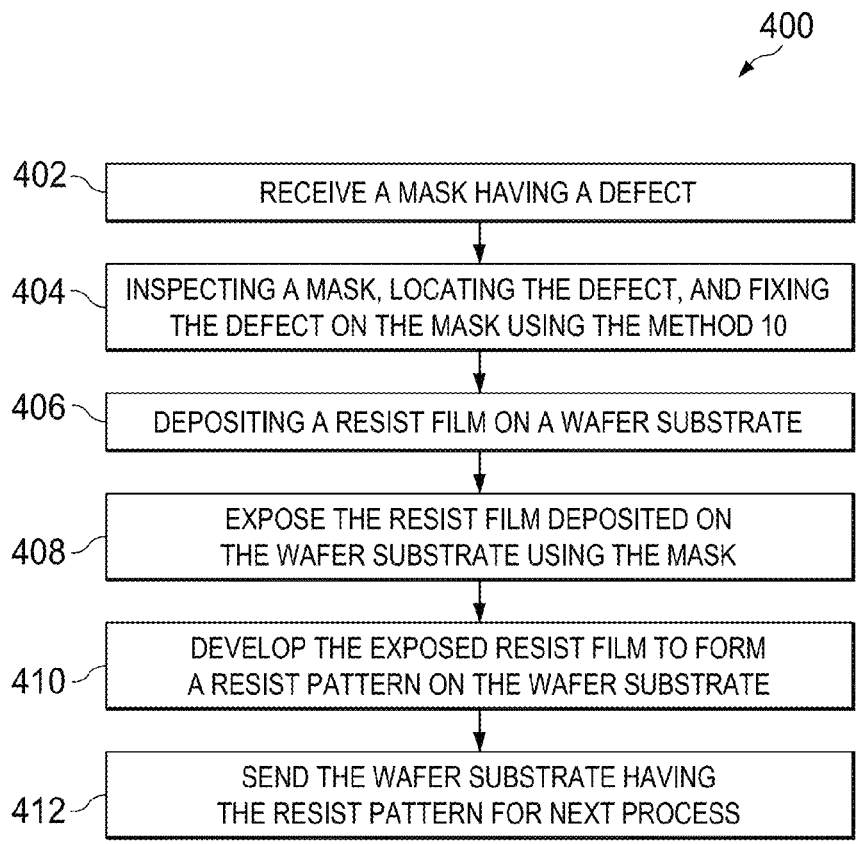
FIG. 9 is a flowchart of a method for fabricating a semiconductor substrate according to one or more embodiments of the present disclosure.

FIG. 9 provides a flowchart of a method 400 for fabricating a device in accordance with various embodiments of the present disclosure. It is understood that additional steps can be provided before, during, and after the method 400, and some steps described can be replaced, eliminated, or moved around for additional embodiments of the method. The method 400 will be further described below, and more specific embodiments of forming a device 500 using the method 400 will concurrently be described with reference to FIGS. 10-14. The method 400 is an example, and is not intended to limit the present disclosure beyond what is explicitly recited in the claims.

Figure 10:
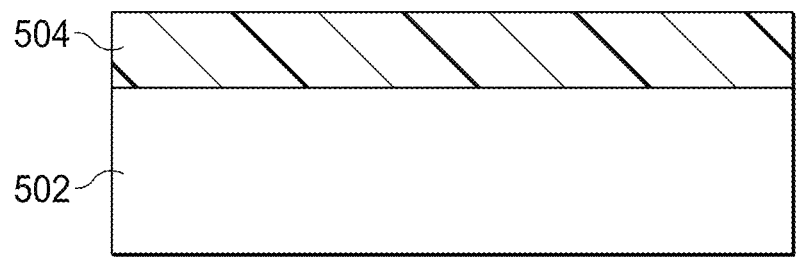
FIGS. 10-14 illustrate sectional views of a semiconductor substrate at various fabrication stages.
Figure 11:
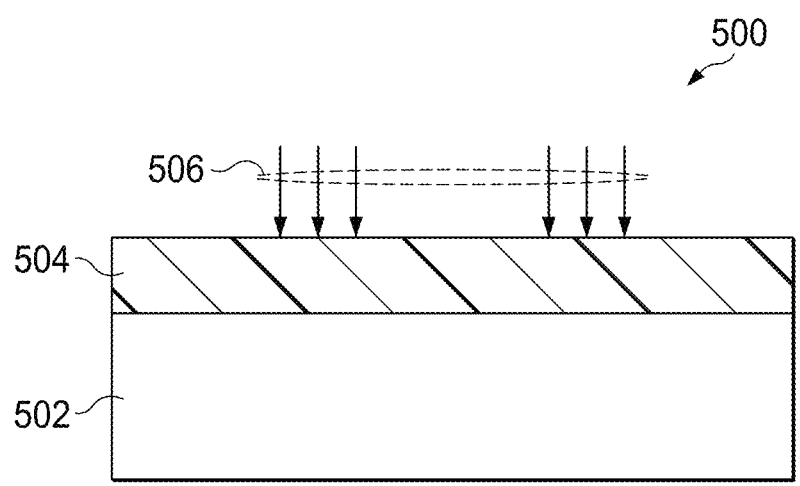

The method 400 begins at step 402 by receiving or providing a wafer substrate. Referring now to FIG. 10, a wafer substrate 502 is provided. In some embodiments, the wafer substrate 502 may include a silicon wafer. Alternatively or additionally, the wafer substrate 502 includes another elementary semiconductor, such as germanium; a compound semiconductor including silicon carbide, gallium arsenic, gallium phosphide, indium phosphide, indium arsenide, and/or indium antimonide; or an alloy semiconductor including SiGe, GaAsP, AlInAs, AlGaAs, GaInAs, GaInP, and/or GaInAsP. In yet another alternative, the wafer substrate 502 includes a semiconductor on insulator (SOI) structure. In other embodiments, the wafer substrate 502 also includes one or more conductive and/or dielectric films. In some embodiments, the dielectric film may include silicon oxide, high k dielectric material film, or a combination of silicon oxide and high k dielectric material, and the conductive thin film for the gate electrode film may include doped polysilicon, or a metal, such as aluminum (Al), copper (Cu), tungsten (W), nickel (Ni), titanium (Ti), gold (Au), platinum (Pt) or alloy of the metals thereof.

The method 400 proceeds to step 404 by inspecting a mask using the method 10 as shown in FIG. 1. In some embodiments, inspecting the mask includes scanning the mask using a mask inspection tool to locate a feature having a defect, repairing the defect on the feature using a mask repair tool, and validating if the defect on the feature is repaired. In some embodiments, validating the repaired feature includes acquiring the DO images of the repaired feature and the reference feature using a point source, and comparing between the DO images of the repaired feature and the reference feature for a DO image difference. If the DO image difference is less than the specification limit, the defect on the feature is repaired. If the DO image difference is greater than the specification limit, the mask needs to be reworked until the defect is repaired.

The method 400 proceeds to step 406 by depositing a resist film on a wafer substrate. Referring again to FIG. 10, a resist film 504 is deposited on wafer substrate 502. In some embodiments, a resist is also referred to as a photo resist. The resist film 504 may include a positive resist or a negative resist. The resist film 504 may include a single layer resist film or a multiple layer resist film. Depositing the resist film 504 on the wafer substrate 502 includes using a coating process, for example a spin-on process. Depositing the resist film 504 includes performing a dehydration process before applying the resist on the substrate, which can enhance an adhesion of the resist film to the wafer substrate. The dehydration process may include baking the wafer substrate at a high temperature for duration of time, or applying a chemical such as hexamethyldisilizane (HMDS) to the substrate. Depositing the resist film 504 also includes a soft bake (SB) process to drive a solvent out of a resist film and increase mechanical strength of a resist film. Depositing the resist film 504 may include applying an antireflective coating, such as a bottom antireflective coating (BARC) or a top antireflective coating (TARC).

The method 400 proceeds to step 408 by exposing a resist film deposited on a wafer substrate. Referring now to the FIG. 11, the resist film 504 deposited on the wafer substrate 502 is exposed by a patterned radiation beam 506. In some embodiments, the patterned radiation beam 506 is generated according to a mask. In other embodiments, the patterned radiation beam 506 is generated according to a mask having a defect repaired using the method 10.

Figure 12:
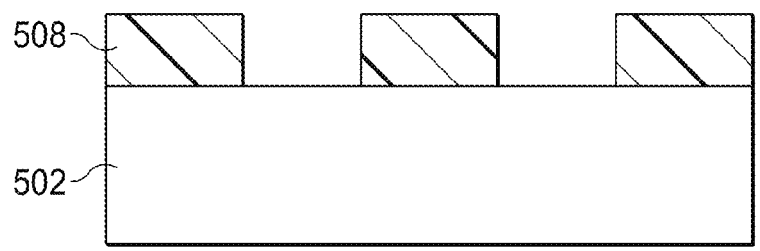

The method 400 proceeds to step 410 by applying a developer on the exposed resist film deposited on the wafer substrate to form a resist pattern on the wafer substrate. Referring now to FIG. 12, a resist pattern 508 is formed on the wafer substrate 502. In some embodiments, a developer includes a water based developer, such as tetramethylammonium hydroxide (TMAH), for a positive tone development (PTD). In other embodiments, a developer may include an organic solvent or a mixture of organic solvents, such as methyl a-amyl ketone (MAK) or a mixture involving the MAK, for a negative tome development (NTD). Applying a developer includes spraying a developer on the exposed resist film, for example by a spin-on process. Applying a developer also include using a post exposure bake (PEB), a post develop bake (PDB) process, or a combination thereof.

Figure 13:
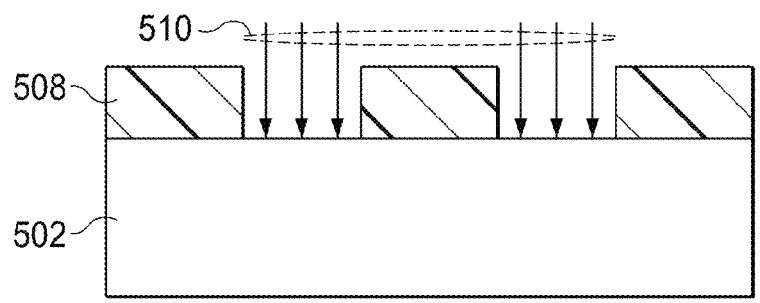
Figure 14:
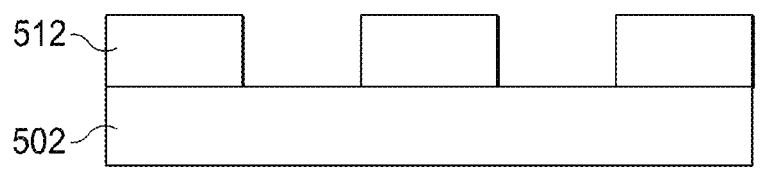

The method 400 proceeds to step 412 by moving the wafer substrate having a resist pattern for executing a subsequent fabrication process. In some embodiments, executing the subsequent fabrication process includes performing an implant process to form a well or a source/drain on the wafer substrate. Referring now to FIG. 13, an ion beam 510 is applied on a selective area of the wafer substrate 502 defined by the resist pattern 508. In other embodiments, executing the subsequent fabrication process includes performing an etching process to transfer the resist pattern into the wafer substrate to form a substrate pattern or feature on the wafer substrate. Referring now to FIG. 14, a substrate feature 512 is formed on the wafer substrate.

The present disclosed method provides various advantages in various embodiments. In some embodiments, the DO images include a plurality of diffraction images from various point sources such that DO images have enough information for validating analysis. In other embodiments, the point sources can be properly chosen such that the corresponding DO images are more sensitive to the characteristics of the repaired defect and therefore more effective to validate the repaired feature. In yet other embodiments, as the DO images include 3D information of the repaired feature, various characteristic aspects, including height, can be effectively evaluated. In yet other embodiments, by DO images, the effect of mask is able to be effectively separated from the effect of the optical component, such as through comparing various intensities and numerical apertures between the repaired feature and the reference feature. Since the optical effect has a same fingerprint in both DO images of the repaired feature and the reference feature, so it can be effectively excluded through comparing.

Thus, the present disclosure provides embodiments of a method of repairing a mask. The method includes inspecting a mask using a mask inspection tool to identify a defect on a circuit pattern of the mask; repairing the defect using a mask repair tool to form a repaired pattern; forming a first group of diffraction images of the repaired pattern and a second group of diffraction images of a reference feature; and validating the mask by comparing the first group of diffraction images with the second group of diffraction images.

The present disclosure also provides other embodiments of a method. The method includes receiving a mask having a first feature with a defect and a second feature; inspecting the mask using a mask inspection tool to locate the defect; repairing the defect using a mask repair tool, resulting in a repaired first feature; forming a first diffraction image of the repaired first feature using a point source; forming a second diffraction image of the second feature using the point source; and validating the repaired first feature by comparing the first diffraction image with the second diffraction image.

The present disclosure also provides other embodiments of a method for fabricating an integrated circuit. The method includes receiving a mask; repairing a feature with a defect; and forming a patterned resist layer on a semiconductor wafer by a lithography process using the mask. The repairing a feature includes inspecting the mask to locate the defect; repairing the defect on the feature; and validating the repaired feature using a diffraction image of the repaired feature.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A method of repairing a mask, the method comprising:
   inspecting the mask using a mask inspection tool to identify a defect on a circuit pattern of the mask;
   repairing the defect using a mask repair tool to form a repaired pattern;
   forming, using a point source, a first group of diffraction images of the repaired pattern and a second group of diffraction images of a reference feature; and
   validating the mask by comparing the first group of diffraction images with the second group of diffraction images.

2. The method of claim 1, wherein the first group of diffraction images includes a first diffraction image from the point source; and
   the second group of diffraction images includes a second diffraction image from the point source.

3. The method of claim 2, wherein
   the first diffraction image includes a first plurality of diffraction order images;
   the second diffraction image includes a second plurality of diffraction order images; and
   the validating the mask includes comparing first intensities and numerical apertures of the first plurality of diffraction order images to second intensities and numerical apertures of the second plurality of diffraction order images, respectively.

4. The method of claim 3, wherein the first plurality of diffraction order images includes zero order, first order, and second order diffraction images.

5. The method of claim 3, wherein the validating the mask includes evaluating differences between the first intensities and numerical apertures of the first plurality of diffraction order images and the second intensities and numerical apertures of the second plurality of diffraction order images, respectively according to predefined criteria.

6. The method of claim 1, wherein the forming the first group of diffraction images of the repaired pattern and the second group of diffraction images of the reference feature includes:
   forming first two diffraction images of the repaired pattern using a first point source and a second point source, respectively; and
   forming second two diffraction images of the reference feature using the first point source and the second point source, respectively.

7. The method of claim 6, wherein the first and second point sources are a pair of symmetric point sources.

8. The method of claim 6, wherein the validating the mask includes comparing first respective intensities and numerical apertures of the first two diffraction images to second respective intensities and numerical apertures of the second two diffraction images.

9. The method of claim 1, wherein the reference feature is a defect-free pattern on the mask.

10. The method of claim 9, wherein the circuit pattern and the reference feature are the same by design.

11. The method of claim 9, wherein
    the circuit pattern includes a first feature where the defect is located;
    the reference feature includes a second feature; and
    the first feature and the second feature have a same dimension by design.

12. The method of claim 1, wherein the mask includes a mask selected from the group consisting of a binary mask, a phase shift mask, and a reflective mask.

13. A method, comprising:
    receiving a mask having a first feature with a defect and a second feature;
    inspecting the mask using a mask inspection tool to locate the defect;
    repairing the defect using a mask repair tool, resulting in a repaired first feature;
    forming a first diffraction image of the repaired first feature using a first point source;
    forming a second diffraction image of the second feature using the first point source; and
    validating the repaired first feature by comparing the first diffraction image with the second diffraction image.

14. The method of claim 13, wherein
    the first diffraction image includes a first plurality of diffraction order images;
    the second diffraction image includes a second plurality of diffraction order images; and
    the validating the repaired first feature includes comparing first intensities and numerical apertures of the first plurality of diffraction order images to second intensities and numerical apertures of the second plurality of diffraction order images, respectively.

15. The method of claim 14, wherein the validating the repaired first feature includes evaluating differences between the first intensities and numerical apertures of the first plurality of diffraction order images and the second intensities and numerical apertures of the second plurality of diffraction order images, respectively according to predefined criteria, and wherein the repaired first feature is validated if the differences are within the predefined criteria.

16. The method of claim 13, further comprising:
   forming a third diffraction image of the repaired first feature using a second point source; and
   forming a fourth diffraction image of the second feature using the second point source,
   wherein the validating the repaired first feature further includes comparing the third diffraction image to the fourth diffraction image.

17. The method of claim 13, wherein the first feature and the second feature have the same dimension by design.

18. The method of claim 13, further comprising patterning a semiconductor wafer using the mask in a lithography process.

19. A method of repairing a mask, the method comprising:
   identifying a defect on a circuit pattern of the mask;
   repairing the defect to form a repaired pattern;
   forming, using a point source, a first group of diffraction images of the repaired pattern and a second group of diffraction images of a reference feature; and
   validating the mask by comparing the first group of diffraction images with the second group of diffraction images.

20. The method of claim 19, wherein the first group of diffraction images includes a first diffraction image from the point source; and
   the second group of diffraction images includes a second diffraction image from the point source.

* * * * *